United States Patent [19]
Kaseda

[11] Patent Number: 5,792,177
[45] Date of Patent: Aug. 11, 1998

[54] FORCEPS

[76] Inventor: Shizuka Kaseda, 6-37-3-407, Minamisenju, Arakawa-ku, Tokyo, 116, Japan

[21] Appl. No.: 685,525

[22] Filed: Jul. 24, 1996

[30] Foreign Application Priority Data

Apr. 1, 1996 [JP] Japan .................... 8-101875

[51] Int. Cl.⁶ .................................. A61B 17/28
[52] U.S. Cl. ............................ 606/205; 606/148
[58] Field of Search ................... 606/139, 144, 606/148, 151, 143, 205, 206, 207

[56] References Cited

U.S. PATENT DOCUMENTS

| | | | |
|---|---|---|---|
| 1,940,351 | 12/1933 | Howard | 606/139 |
| 3,841,521 | 10/1974 | Jarvik | 221/75 |
| 5,217,471 | 6/1993 | Burkhart | 606/148 |
| 5,318,579 | 6/1994 | Chow | 606/148 |
| 5,454,820 | 10/1995 | Kammerer et al. | 606/148 |
| 5,462,562 | 10/1995 | Elkus | 606/148 |

FOREIGN PATENT DOCUMENTS

| | | |
|---|---|---|
| 0 567 146 A2 | 10/1993 | European Pat. Off. |
| 0 621 009 A1 | 10/1994 | European Pat. Off. |
| 41 27 812 A1 | 2/1993 | Germany . |
| 7-9311(U) | 2/1995 | Japan . |

*Primary Examiner*—Michael Buiz
*Assistant Examiner*—Kevin Truong
*Attorney, Agent, or Firm*—Kubovcik & Kubovcik

[57] ABSTRACT

There is provided a forcepts providing for positive and rapid ligation in surgery. The forceps comprises a manual actuator, a grasping members connected to the actuator through a body member and including two grasping members adapted to open or close in response to the corresponding action of the actuator, and a suture guide stationary with respect to the body member or either one of the grasping members, the suture guide being adapted to engage a suture and guide it to a space within reach of the grasping members.

17 Claims, 8 Drawing Sheets

FORCEPS

TECHNICAL FIELD

The present invention relates to forceps and more particularly to a forceps providing for rapid and positive ligation in surgical procedures.

BACKGROUND OF THE INVENTION

This application claims the priority of a Japanese Patent Application Serial No. 8-101875 filed on Apr. 1, 1996.

BRIEF DESCRIPTION OF THE PRIOR ART

In surgery, several to scores of ligations (tying blood vessels etc.) are performed per operation. Ligation is carried out by passing a surgical suture to a ligation site, making a knot, and pulling both ends of the knot in opposite directions.

The recent trend in surgery is towards reducing the incision or notch breadth so as to reduce the postoperative burden on the patient. By way of illustration, the incision breadth is generally about 2 cm in endoscopic and thoracoscopic surgeries and about 10 cm in mini-thoracotomy.

In a surgical operation involving such a small-breadth incision, it is difficult to make a knot within the body cavity and, therefore, it is common practice to form a provisional knot outside the body cavity and push the knot into the cavity with the aid of a known exclusive device generally referred to as a knot pusher. Thus, the general ligation method comprises feeding such an extracorporeally formed provisional knot into the patient's notch and pulling one end or both ends of the knot with the grasping tips of a forceps.

However, the conventional ligation procedure described above is not only complicated but also time-consuming because the forceps for grasping the knot and pulling the suture can be inserted from the wound opening into the body cavity only after said knot pusher has been withdrawn. In surgical operations in which time is of vital importance, it is undesirable to waste time for ligation even if it is a matter of seconds.

To overcome the above disadvantages of the conventional ligation procedure, an improved ligation technique has recently been proposed in which, with two ends of the suture extending from a knot being lodged in grooves cut in the peripheral walls of the two grasping tips of a forceps, the knot is fed into the body cavity for ligating. By this ligation technique, a ligation can be effected using a forceps alone so that the ligation can be accomplished in a relatively short time.

However, it has been pointed out by surgeons that with the above grooved forceps, the suture tends to be dislodged from the grooves in the course of pushing the knot. Therefore, depending on the status of operation, it becomes necessary to re-lodge the suture in said grooves a few times before completing a ligation so that the knot cannot be fed quickly and accurately into the body cavity.

Having been developed in view of the above-described state of the art, the present invention has for its object to provide a forceps which enables the surgeon to effect ligation positively and quickly.

SUMMARY OF THE INVENTION

The forceps of the invention recited in claim 1 appended to this specification comprises a manual actuator, a grasping means operatively connected to said actuator directly or through a body member and adapted to open or close in response to an action of said actuator, and a suture guide adapted to engage a suture and guide it into a space within reach of said grasping means.

The forceps of the invention recited in claim 6 comprises a manual actuator, a grasping means operatively connected to said actuator through a body member and having two grasping members adapted to open or close in response to an action of said actuator, and a suture guide stationary with respect to either said body member or one of said grasping members and adapted to engage a suture and guide it into a space within reach of said grasping means.

In the forceps of the inventions recited in claims 2 and 7, said suture guide comprises an arm member and a ring member rigidly secured to a forward end of said arm member for passage of said suture therethrough.

In the forceps of the inventions recited in claims 3 and 8, said ring member comprises a closed ring.

In the forceps of the inventions recited in claims 4 and 9, said ring member has a suture inlet defined by resiliently splayable edges on its circumference to radially admit said suture.

In the forceps of the inventions recited in claims 5 and 10, a grasping plane traced by said grasping means is angled with respect to the longitudinal axis of said body member and said ring member is disposed on the same side as said actuator with respect to the position of said grasping means.

As the suture is passed into the ring member of the suture guide, the suture is guided into a space within reach of the grasping means. Once a knot is thus formed just under the grasping means, it can be easily pushed down with the open grasping means. Preferably, the grasping means is set in a nearly closed condition just precluding slip-out of the knot and the knot is pushed down into the body cavity with the grasping means held in that condition. Of course, even if the knot happens to pass through the grasping means, it can be pushed with the ring member.

Even after the knot has been pushed into the body cavity, one extension of the knot is invariably in the space within reach of the grasping means. Therefore, the extension of the knot fed into the body cavity can be positively grasped to effect ligation with utmost certainty. Moreover, feeding of the knot into the body cavity and grasping of one extension of the knot can be carried out with a single forceps, with the result that quick ligation becomes feasible.

DETAILED DESCRIPTION OF THE PREFERRED EMBODIMENTS OF THE INVENTION

The present invention is now described in detail with reference to the accompanying drawings which show several preferred embodiments of the invention. It should be understood, however, that the embodiments illustrated and described are merely illustrative and that many changes and modifications may be made by those skilled in the art without departing from the spirit and scope of the invention as recited in the appended claims.

Figure 1:
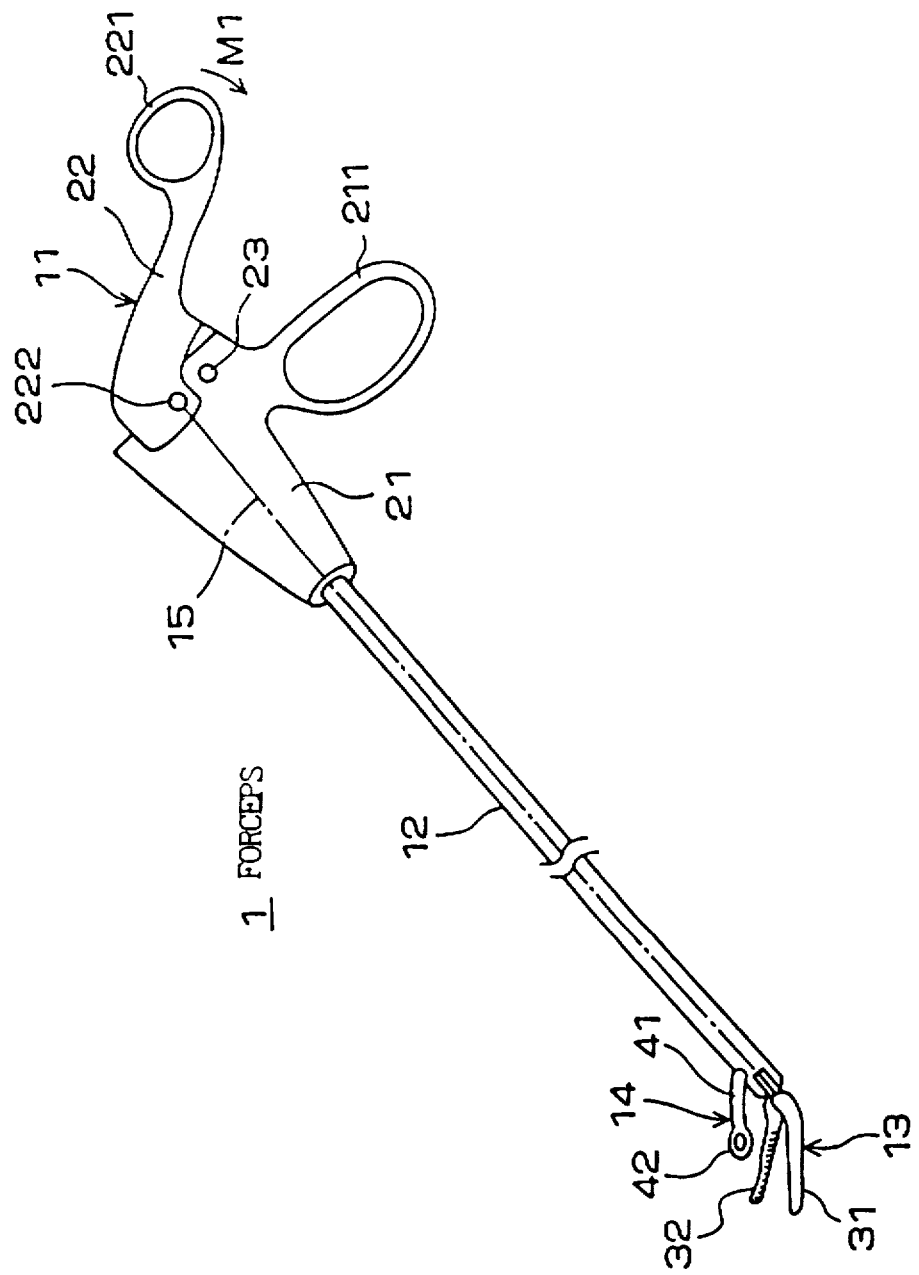
FIG. 1 is a perspective view of a forceps 1 according to the present invention.
Figure 2:
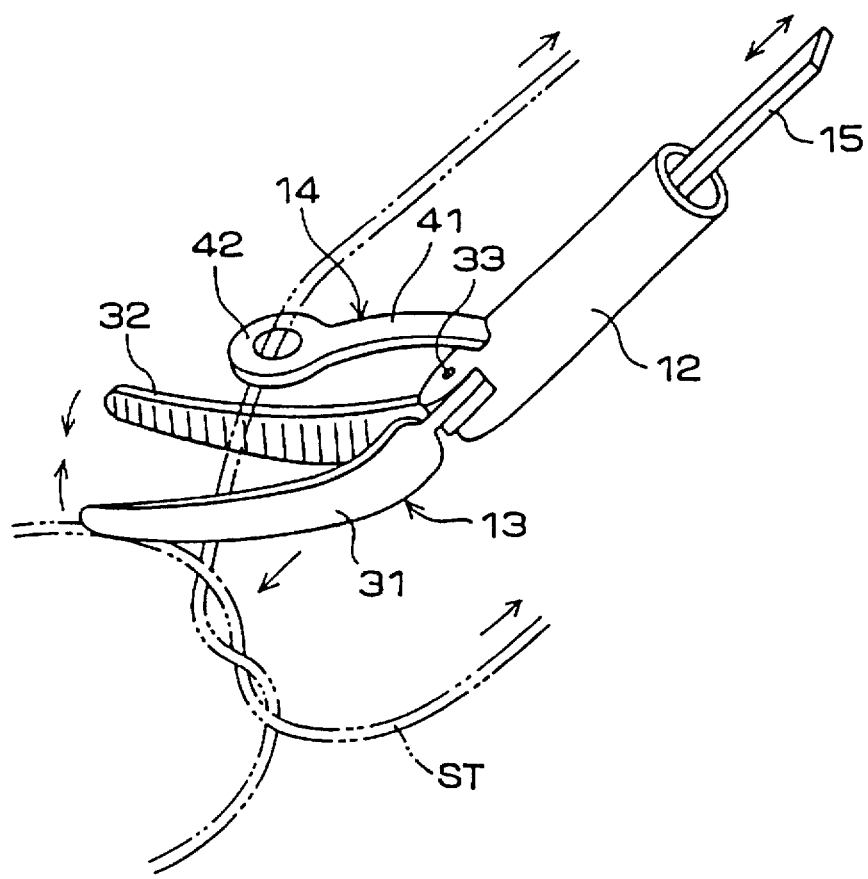
FIG. 2 is a view showing the tip portion of said forceps 1 on exaggerated scale.
Figure 3:
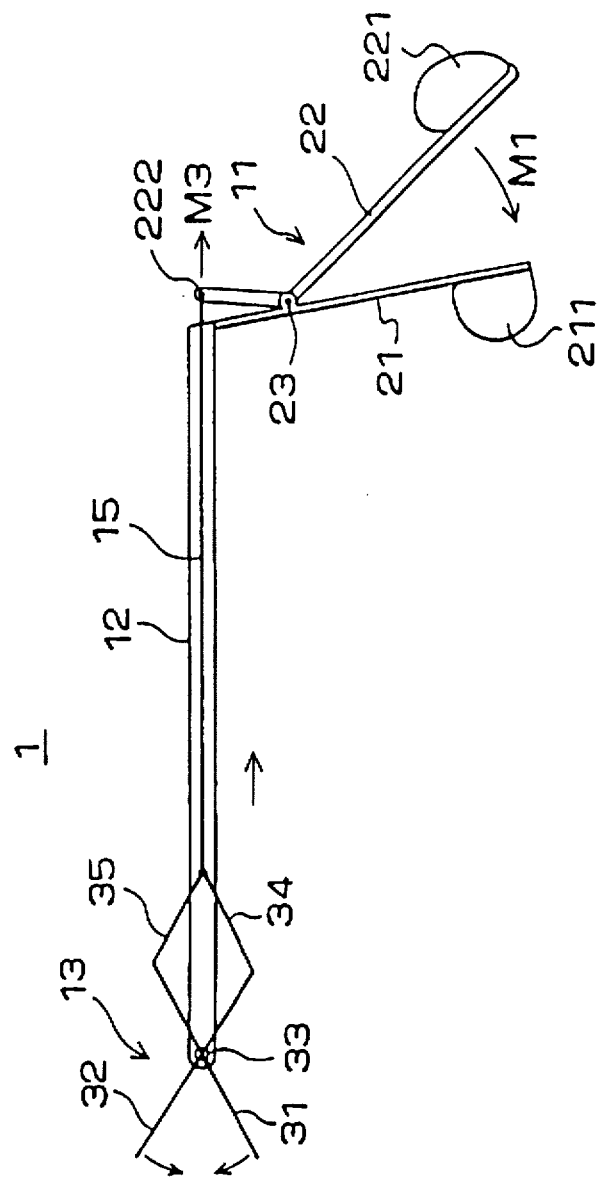
FIG. 3 is a view illustrating the mechanism of action of forceps 1.

Referring to FIGS. 1-3 and particularly to FIG. 1, a forceps 1 comprises an actuator 11, a body member 12, a grasping means 13, and a suture guide 14.

The actuator 11 comprises an actuator base 21 and a rotary member 22 which is rotatable about a pivotal shaft 23 with respect to said actuator base 21. The actuator 11 can be molded from a synthetic resin material or die-formed from a metallic material. The actuator base 21 and the rotary member 22 are provided with finger-grip means 211 and 221, respectively, for accepting the surgeon's fingers. The rotary member 22 is further provided with a pin 222, to which a rod 15 is connected for transmitting the torque of the rotary member 22 to open or close the grasping means 13.

Thus, the actuator 11 is manually operated. When the rotary member 22 is rotated in the direction indicated by arrowmark M1 for instance, the pin 222 is displaced in the direction indicated by arrowmark M3 about the pivot 23 to pull the rod 15.

The body member 12 is a tubular element made of metal such as titanium or stainless steel. One end of the body member 12 is supported in the base 21 of the actuator 11 in such a manner that while it is free to turn in the circumferential direction, its relative movement in the axial direction is precluded. The actuator base 21 is further provided with a knob (not shown) for rotating the body member 12. The body member 12 and the actuator 11 may be rigidly secured to each other, thus precluding their relative movement.

Referring to FIG. 2, too, the grasping means 13 comprises two grasping members 31 and 32 which are rotatable about a pin 33 secured to a forward end portion of the body member 12. The opposed inner surfaces of the grasping members 31, 32 are respectively formed with stripe-shaped grooves for preventing slippage of the load grasped. These surfaces may be formed with mesh-like grooves instead of stripe-shaped grooves.

As shown in FIG. 3, the rear ends of said grasping members 31, 32 are rotatably connected to the forward ends of links 34, 35 which are located in said body member 12. The other ends of links 34, 35 are rotatably connected to each other and the forward end of said rod 15 is rotatably connected to the same ends. Therefore, as the rod 15 moves in the axial direction, the grasping members 31, 32 undergo an opening or a closing action via links 34, 35. In other words, the grasping means 13 opens or closes in response to the action of the actuator 11.

As best seen in FIGS. 1 and 2, the grasping plane which is the plane constituted by the opening or closing action of grasping members 31, 32 has an angle with respect to the longitudinal axis of the body member 12. Therefore, with the grasping means 13, not only an object lying on an extension of the axis of the body member 12 but also an object lying offset from said extension can be grasped. In other words, the surgical suture ST can be easily grasped. Incidentally, the grasping means 31, 32 and the rod 15 are respectively made of metal such as titanium or stainless steel.

The suture guide 14 comprises an arm member 41 and a ring member 42 disposed at a forward end of said arm member 41 for allowing passage of the suture ST therethrough. This suture guide 14 is a one-piece element formed from a metal material such as titanium or stainless steel and is rigidly secured to the body member 12 by a fastening means, such as welding, in a position such that the ring member 42 will lie on the same side as the actuator 11 with respect to the position of grasping means 13 and the suture ST to be passed through the ring member 42 will be guided into a space within reach of the grasping means 13.

The inner diameter of the ring member 42 can be sufficiently large to easily accept the surgical suture ST to be used. For example, when a silk suture sized 1-0, 2-0, or 3-0 is used as said suture material ST, the inner diameter of ring member 42 can be about a few fractions of one millimeter to a few millimeters. The inner peripheral surface of ring member 42 should be smoothened to allow uninterrupted passage of suture ST.

The forceps 1 described above is of a type such that the finger-grips 211, 221 of the actuator 11 are disposed on one side of the longitudinal axis of the body member 12. However, it may be so arranged that the finger-grips 211, 212 will be disposed in mutually symmetric relation about said axis of body member 12. Furthermore, the grasping means 13 described above may be of the double-acting type in which both grasping members 31, 32 are actuated to open and close the forceps or it may be of the single-acting type such that either one of grasping members 31, 32 opens and closes the forceps.

Figure 4:
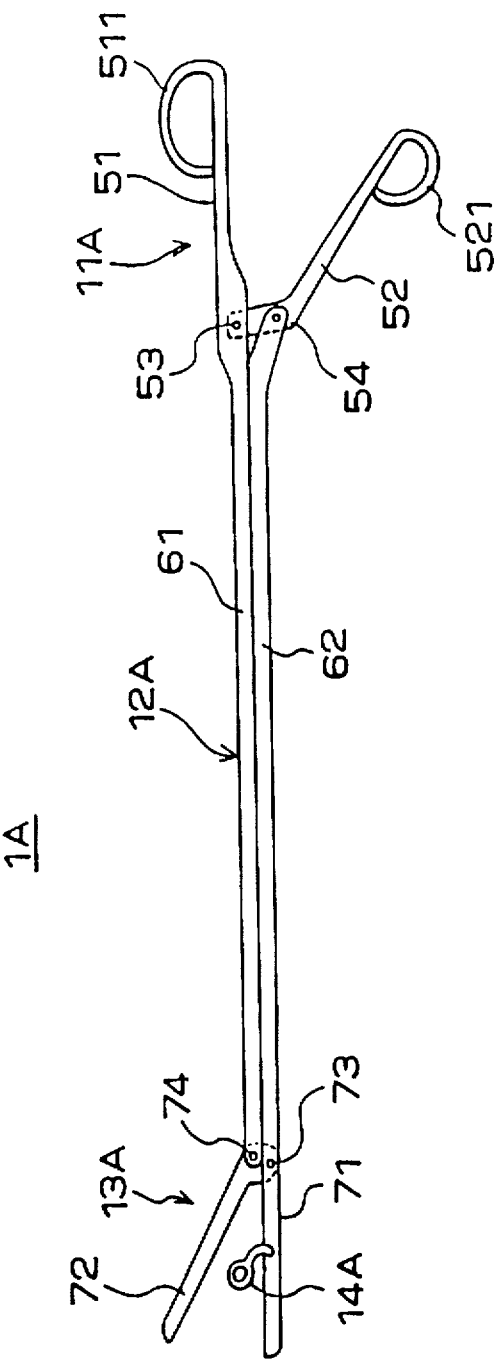
FIG. 4 is a front view of a forceps according to another embodiment of the present invention.

FIG. 4 is a front view of a forceps 1A according to another embodiment of the present invention.

Referring to FIG. 4, this forceps 1A comprises an actuator 11A, a body member 12A, a grasping means 13A, and a suture guide 14A.

The actuator 11A comprises an actuator base 51 integral with a body portion 61 of the body member 12A and an actuator rotary member 52 disposed rotatably about a pivot 53 with respect to said actuator base 51. The actuator base 51 and rotary member 52 are equipped with finger-grips 511, 521, respectively. The actuator rotary member 52 carries a pin 54 to which a rear end of another body portion 62 of said body member 2A is rotatably mounted.

One of grasping members 71 of said grasping means 13A is integral with the body member 62. The other grasping member 72 of grasping means 13A has one end rotatably connected to a pin 73 of said body member 62 near the base of the grasping member 71 and is rotatably connected by a pin 74 to a forward end of said body member 61 in the neighborhood of pin 73.

The suture guide 14A is rigidly secured to the grasping member 71 in an approximate center of its length.

This forceps 1A performs its opening and closing actions in the following manner. As the actuator 11A is manipulated, the body portion 62 slides axially with respect to the body portion 61, whereupon the pin 73 and pin 74 are relatively displaced to drive the grasping member 72 to open or close the forceps 1A. In this embodiment, the forceps 1A is single-acting. The free end portions of said grasping member 71 and grasping member 72 may be respectively bent at an angle with respect to the axial direction of the body portions 61 and 62 and said suture guide 14A be disposed within the grasping plane formed by the bent portions. By bending the end portions in this way, feeding of a suture knot by the grasping member 71 or 72 is facilitated.

Figure 5:
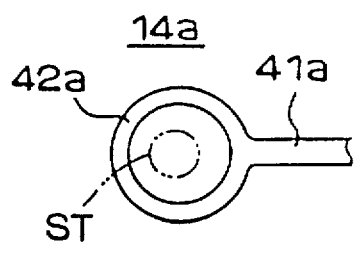
FIG. 5 show various ring members for the suture guide.
Figure 5:
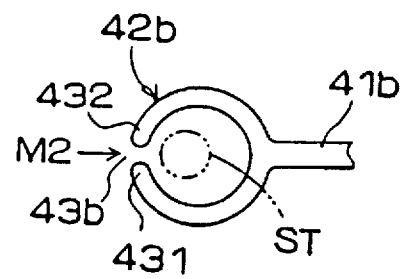
Figure 5:
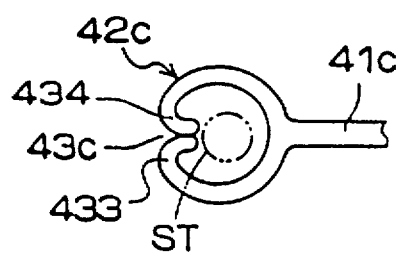
Figure 5:
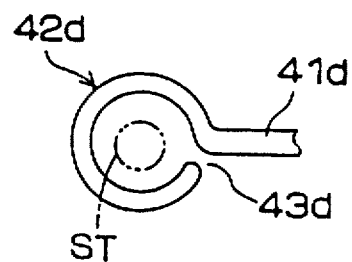
Figure 5:
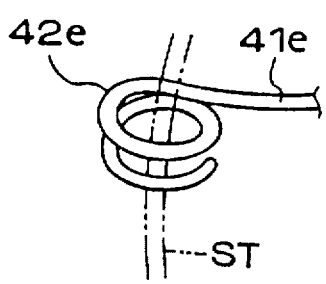
Figure 5:
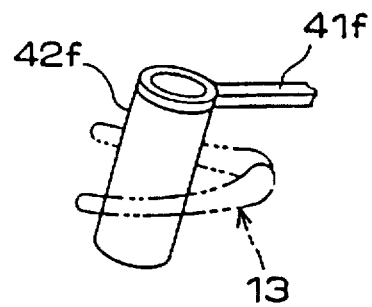

FIG. 5 shows various ring members 42a-f for suture guide 14 or 14A.

FIGS. 5(A)-(D) are front views of ring members 42a-42d, and FIGS. 5(E) and (F) are perspective views of ring members 42e and 42f. The ring members 42a-e are made of a resilient metallic material or synthetic resin.

The ring member 42a shown in FIG. 5(A) is a closed ring similar to the ring member described for forceps 1 and 1A. When this ring member 42a is employed, the suture ST must be passed into the ring from its free end but the surgical suture ST once passed is never disengaged from the ring member 42a.

The ring member 42b shown in FIG. 5(B) has a suture inlet 43b defined by its edges 431, 432 resiliently retreatable from each other in its circumferential direction, and through this suture inlet 43b, the suture ST can be inserted into the ring member 42b by biasing the suture in the radial direction (arrowmark M2) of the ring.

When the suture ST is supplied to the suture inlet 43b, the edges 431, 432 are urged apart because of the inherent resiliency of the ring member material and the suture ST itself is transiently reduced in diameter under the compressive force applied by the edges 431, 432 so that it is admitted into the ring 42b. Therefore, when this ring member 42b is adopted, the suture ST can be easily inserted into the ring 42b via said suture inlet 43b by urging the suture ST in the radial direction of the ring.

The edges 431 and 432 may be normally in contact with each other or be slightly splayed but they should be finished to present smooth surfaces for facilitating passage of the suture ST and protecting ST against damage. When a non-resilient material is used for the ring member 42b, the edges 431 and 432 can be positioned away from each other by a distance smaller than the diameter of the suture ST so that the suture may be admitted through the suture inlet 43b as it is compressed in the direction of its diameter.

The ring member 42c shown in FIG. 5(C) is also equipped with a suture inlet 43c similar to that of ring member 42b. In this ring member 42c, however, the edges 433, 434 are bent inwardly of the ring member 42c so as to facilitate insertion of the suture ST. Because the edges 433, 434 are thus inwardly bent, the suture once inserted into the ring member 42c cannot easily go out of the ring 42c.

The ring member 42d shown in FIG. 5(D) is provided with a suture inlet 43d in a position adjacent to the point of its transition to the arm 41d.

The ring member 42e shown in FIG. 5(E) has a spiral form. When this ring member 42e is adopted, the suture ST can be easily inserted into the ring 42e by passing the suture ST along an arm member 41e towards the ring member 42e and, after contact with the ring 42e, turning the lower part of the suture ST along the outer periphery of the ring 42e.

The ring member 42f shown in FIG. 5(F) is a flexible cylindrical tube made of, for example, synthetic resin. As the grasping means 13 is closed with the suture ST entrapped in the ring member 42f, the ring member 42f is flexed to grasp the suture ST as well. For use of this ring member 42f, an arm 41f may be provided at either end.

The procedure for ligating with the above-described forceps 1 of the invention in a surgical operation is now described with reference to FIGS. 6–8.

Figure 6:
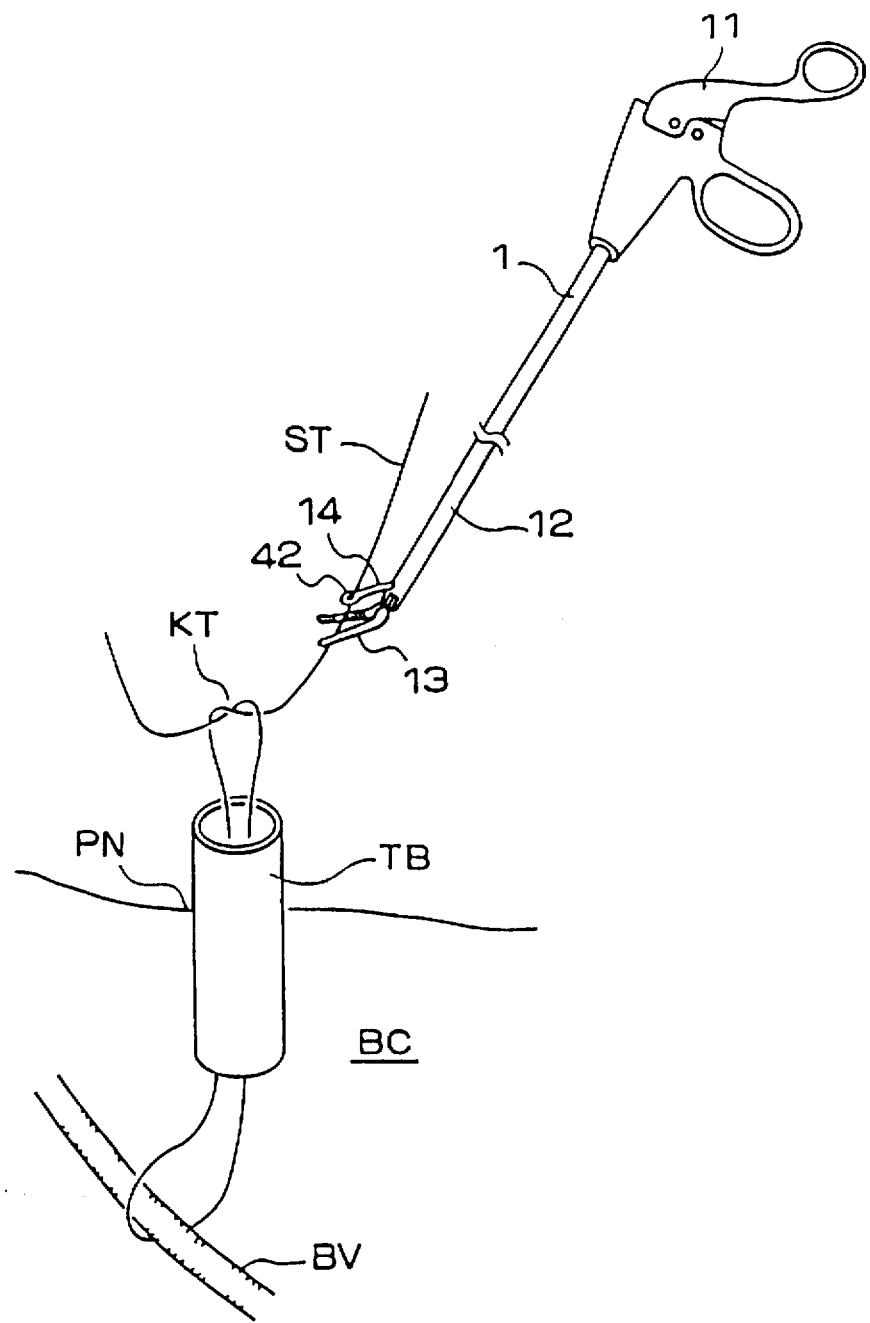
FIG. 6 is a view showing an extracorporeally formed provisional knot immediately before insertion into the body cavity.
Figure 7:
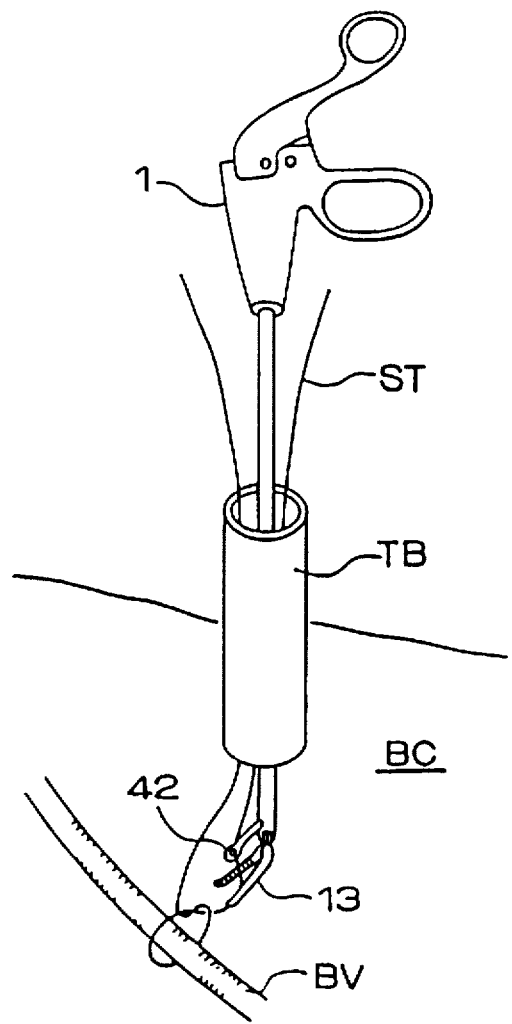
FIG. 7 is a view showing the same knot fed into the body cavity.

FIG. 6 is a view showing an extracorporeally formed knot KT immediately before insertion into the body cavity BC; FIG. 7 is a view showing the same knot KT fed into the body cavity BC; and FIG. 8 is a view showing a ligation being effected. It should be noted that these are merely schematic views and inaccurate in dimensional relationship.

As illustrated in FIG. 6, a tube TB has been inserted into the patient's notch PN and the suture material ST fed through the tube TB has been looped a single turn around the blood vessel BV. This status can be established typically in the following manner. For example, one end of the suture ST is inserted from the notch PN into the body cavity BC and after it is looped around the ligation site of the blood vessel BV, the suture end is retrieved out of the body cavity BC. Then, both ends of the suture ST are pulled out from the top of the tube TB and finally the tube TB is fitted into the notch PN.

[Step 1]
First, a provisional knot KT is formed of the suture ST outside the body cavity BC.

[Step 2]
One end of the suture ST is passed through the ring member 42 of the suture guide 14 of forceps 1 from down to up. In this condition, the suture ST passes between the grasping members of the grasping means 13 (FIG. 6) in the open position.

[Step 3]
With both ends of the suture ST being held by fingers to keep the suture substantially taut without an excessive slack, the grasping means 13 of the forceps 1 is closed down to the extent that the suture ST will not be grasped and, yet, the knot KT will not pass therethrough and with the knot KT being pushed by the grasping means 13, the tip of forceps 1 and knot KT are inserted together into the tube TB. In this manner, the knot KT can be fed into the body cavity BC (FIG. 7).

Figure 8:
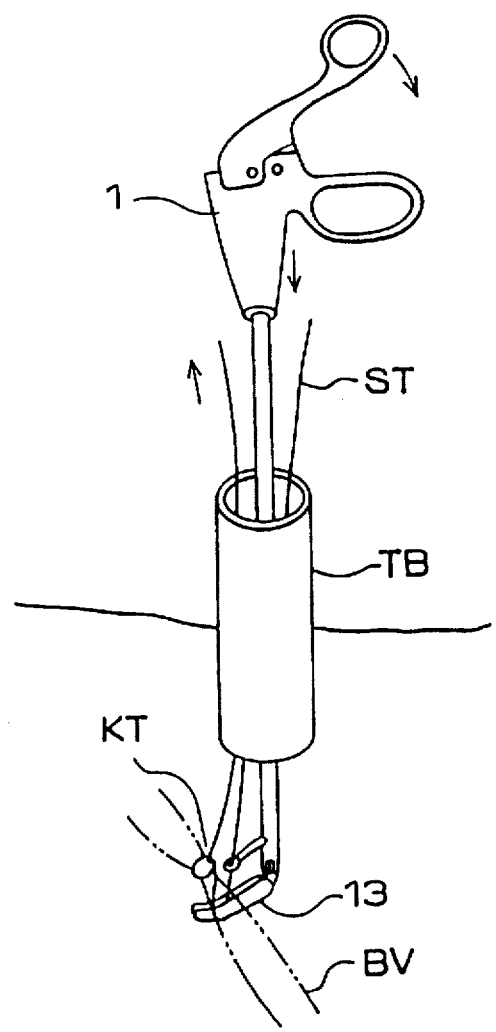
FIG. 8 is a view showing a ligation being effected.

[Step 4]
After the knot KT has been pushed down by the grasping means 13 of the forceps 1 to the neighborhood of blood vessel BV, the grasping means 13 is closed to firmly grasp one end of suture ST extending from the knot KT and the other end of suture ST is grasped by hand outside the body cavity BC and pulled to effect a ligation (FIG. 8).

Instead of grasping and pulling said one end of suture ST by hand, another forceps may be inserted into the body cavity BC via the tube TB and the suture ST be pulled by the two forceps to effect a ligation. In this case, only one forceps needs to have a suture guide.

After completion of ligation, the forceps 1 is withdrawn from the body cavity BC and the suture ST is cut with a suitable cutting means.

The suture ST is passed through the ring member 42 as described above. Therefore, upon closure of the grasping means, the suture ST invariably lies in the space within reach of the grasping means. Therefore, it is easy to push the knot KT down with the grasping means 13 so that the knot KT can be successfully fed into the body cavity BC. Moreover, even if the knot KT has passed the grasping means 13, it will not happen that the knot KT passes the ring member 42, with the result that the knot KT is successfully guided into the body cavity BC by said ring member 42. Thus, with the forceps 1, the knot KT can be fed easily and positively into the body cavity BC. Furthermore, since the suture ST can be securely grasped with the grasping means 13, the suture ST can be firmly grasped to effect a ligation even if the suture ST is out of the surgeon's view at ligation.

The above description of the ligation procedure applies to the use of a forceps 1 equipped with a closed ring member 42. When a forceps equipped with any of the ring members 42b–d having suture inlets 43b–d as illustrated in FIGS. 5(B)–(D) is employed, the ligation procedure is as follows.

In this case, the suture ST need not necessarily be passed into the ring member 42b–d from one of its ends. Thus, the suture ST can be passed through the ring member 42b–d not only outside the body cavity BC but also within BC. One end of the suture ST is pulled to keep it tense and the tense part is abutted against the suture inlet 43b–d, whereby the suture is forced into the ring member 42b–d.

In the above embodiment, the case in which the ring member 42 lies on the same side as the actuator 11 with respect to the position of grasping means 13 has been described but the suture guide 14 may be disposed on the opposite side of the actuator 11. Moreover, the suture guide 14 may be provided on each side. By providing the suture guide 14 on each side, the suture ST can be positively positioned in a space within reach of the grasping means 13 so that a ligation can be positively achieved.

In the above embodiment, the case in which the grasping means 13, 13A was operatively connected to the actuator 11, 11A through a body member 12, 12A has been described but the grasping means 13, 13A may be operatively connected to the actuator 11, 11A directly.

In the above description the arm 41 of the suture guide 14 has been described as being a single rod but it may consist of a plurality of rods or be a plate-shaped member. Moreover, although the suture guide 14 has been described as being welded to the body member 12, it may be secured with an adhesive, cauked tightly into a hole, locked with screw means, or removably connected. Furthermore, the suture guide 14 and body member 12 may be molded one-piece. As the material of suture guide 14, a suitable metal other than those mentioned or a synthetic resin can be employed. The configuration of the grasping means 13 may also be suitably modified. The grasping means 13 may be changed from one kind to another according to the type of grasping load. Furthermore, the construction, shape, size and material of each component part of the forceps 1 may be changed or modified without departing from the spirit and scope of the present invention recited in the appended claims.

According to the present invention as recited in claims 1–3 and claims 6–8, ligations in surgical operations can be carried out positively and rapidly.

According to the present invention as recited in claims 4 and 9, a suture can be easily passed into the ring member of a forceps.

According the present invention as recited in claims 5 and 10, the grasping of a suture by the grasping means of a forceps is further facilitated.

What is claimed is:

1. A forceps comprising a manual actuator, a grasping means operatively connected to said actuator to open and close in response to an action of said actuator, and a suture guide having an opening facing a grasping plane traced by the opening and closing of said grasping means and adapted to engage a suture and guide said suture to a space such that said suture can be grasped by said grasping means.

2. The forceps according to claim 1 wherein said suture guide comprises an arm member and a ring member rigidly secured to a forward end of said arm member for passage of said suture therethrough.

3. The forceps according to claim 2 wherein said ring member comprises a closed ring.

4. The forceps according to claim 3 wherein:

said grasping plane traced by said grasping means is angled with respect to a longitudinal axis of a body member, and said ring member is disposed on the same side as said actuator with respect to the position of said grasping means.

5. The forceps according to claim 2 wherein said ring member has a suture inlet defined by resiliently splayable edges on its circumference to radially admit said suture.

6. The forceps according to claim 5 wherein:

said grasping plane traced by said grasping means is angled with respect to a longitudinal axis of a body member, and said ring member is disposed on the same side as said actuator with respect to the position of said grasping means.

7. The forceps according to claim 2 wherein said grasping plane traced by said grasping means is angled with respect to a longitudinal axis of a body member and said ring member is disposed on the same side as said actuator with respect to the position of said grasping means.

8. The forceps according to claim 1 wherein said grasping means is directly connected to said actuator.

9. The forceps according to claim 1 wherein said grasping means is connected to said actuator through a body member.

10. A forceps comprising a manual actuator, a grasping means operatively connected to said actuator through a body member and having two grasping members adapted to open and close in response to an action of said actuator, and a suture guide stationary with respect to said body member and having an opening facing a grasping plane traced by the opening and closing of said grasping means and adapted to engage a suture and guide said suture into a space such that said suture can be grasped by said grasping means.

11. The forceps according to claim 10 wherein said suture guide comprises an arm member and a ring member rigidly secured to a forward end of said arm member for passage of said suture therethrough.

12. The forceps according to claim 11 wherein said ring member comprises a closed ring.

13. The forceps according to claim 12 wherein:

said grasping plane traced by said grasping means is angled with respect to a longitudinal axis of said body member, and said ring member is disposed on the same side as said actuator with respect to the position of said grasping means.

14. The forceps according to claim 11 wherein said ring member has a suture inlet defined by resiliently splayable edges on its circumference to radially admit said suture.

15. The forceps according to claim 14 wherein:

said grasping plane traced by said grasping means is angled with respect to a longitudinal axis of said body member, and said ring member is disposed on the same side as said actuator with respect to the position of said grasping means.

16. The forceps according claim 11 wherein said grasping plane traced by said grasping means is angled with respect to a longitudinal axis of said body member and said ring member is disposed on the same side as said actuator with respect to the position of said grasping means.

17. A forceps comprising a manual actuator, a grasping means operatively connected to said actuator and having two grasping members adapted to open and close in response to an action of said actuator, and a suture guide stationary with respect to one of said grasping members and having an opening facing a grasping plane traced by the opening and closing of said grasping means and adapted to engage a suture and guide said suture into a space such that said suture can be grasped by said grasping means.

* * * * *